United States Patent [19]

Amano et al.

[11] 4,151,217

[45] Apr. 24, 1979

[54] METHOD OF COOLING CRACKED GASES OF LOW BOILING HYDROCARBONS

[75] Inventors: Kazutoshi Amano, Kobe; Kazuyasu Suehiro, Nishinomiya; Takehiko Sato; Yuuji Ohnishi, both of Yokkaichi, all of Japan

[73] Assignees: Mitsubishi Jukogyo Kabushiki Kaisha; Mitsubishi Petrochemical Company Limited, both of Tokyo, Japan

[21] Appl. No.: 858,455

[22] Filed: Dec. 8, 1977

Related U.S. Application Data

[63] Continuation-in-part of Ser. No. 779,157, Mar. 18, 1977, abandoned, which is a continuation of Ser. No. 628,825, Nov. 4, 1975, abandoned, which is a continuation of Ser. No. 370,614, Jun. 18, 1973, abandoned.

[30] Foreign Application Priority Data

Jul. 4, 1972 [JP] Japan .................................. 47-66321

[51] Int. Cl.² ........................ C07C 11/04; C07C 3/30
[52] U.S. Cl. .............................. 260/683 R; 208/48 Q
[58] Field of Search .................. 260/683 R; 208/48 Q

[56] References Cited

FOREIGN PATENT DOCUMENTS

1087512 10/1967 United Kingdom ................ 260/683 R

Primary Examiner—Delbert E. Gantz
Assistant Examiner—Charles E. Spresser
Attorney, Agent, or Firm—Sherman & Shalloway

[57] ABSTRACT

The formation and accumulation of coke or other reaction by-products of olefins produced by the pyrolysis of hydrocarbons is prevented. This is accomplished by maintaining the transfer portion extending from the outlet port of the pyrolysis reaction tube to the multi-tubular quenching device at a temperature below 450° C. This technique is especially applicable to the manufacture of olefins by the pyrolysis of hydrocarbons which are gaseous at room temperature under atmospheric pressure or liquid hydrocarbons having a volumetric average boiling point of below 90° C., at temperatures ranging from 750° to 900° C., followed by quenching in a multi-tubular quenching apparatus. It is only necessary to cool the transfer portions to a temperature below 450° C. in those areas where cracked gas is flowing at a flow rate below 50 kg/m² per sec.

4 Claims, 6 Drawing Figures

METHOD OF COOLING CRACKED GASES OF LOW BOILING HYDROCARBONS

This application is a continuation-in-part of application Ser. No. 779,157, filed Mar. 18, 1977, now abandoned which in turn is a continuation of application Ser. No. 628,825, filed Nov. 4, 1975, now abandoned, which in turn is a continuation of application Ser. No. 370,614, filed June 18, 1973, now abandoned.

This invention relates to a method manufacturing olefins by pyrolyzing gaseous hydrocarbons or liquid hydrocarbons of a volumetric average boiling point of below 90° C. followed by quick cooling of the high-temperature cracked gases. More particularly, this invention relates to an improved method of quenching the high-temperature cracked gases obtained by the pyrolysis of gaseous or liquid hydrocarbons to temperatures below 450° C. by means of an indirect heat exchanger.

The manufacture of olefins by mixing gaseous hydrocarbons such as ethane, propane, and butane, or completely volatile liquid hydrocarbons having a volumetric average boiling point of below 90° C., such as naptha, with steam, at a temperature ranging from 750° C. to 900° C. in an externally heated reaction tube to pyrolyze the resulting mixture is known. It is also known to avoid undesireable secondary reactions by very quickly cooling the reactive high-temperature cracked gases.

The prior art has taught various methods for rapidly cooling the high-temperature gases. According to one method, the high-temperature cracked gas taken out of the pyrolysis reaction tube is introduced to a cooling device with the cracked gases directly quenched with a coolant, such as liquid hydrocarbon, water or steam. Another method teaches to pass the high-temperature cracked gas supplied from the pyrolysis reaction tube through a multi-tubular indirect quick-cooling heat exchanger to effect indirect cooling.

The direct cooling method, however, has many disadvantages, including, for example, occurrence of coking at the injection port of the coolant, occurrence of thermal stress and mechanical difficulties resulting from the injection of coolant to the high-temperature cracked gas, and loss of unrecoverable heat energy possessed by the high-temperature cracked gas.

The indirect cooling method permits some improvement in recovery of heat as compared to the direct cooling method. However, the indirect cooling still does not prevent occurrence of coking in the path from the outlet port of the pyrolysis reaction tube to the portion in the cooling device where the cracked gas will be cooled. In a modification of indirect quick-cooling technique using a multi-tubular heat exchanger, a distribution chamber—a space provided at the entrance of the heat exchanger to distribute the cracked gas into a number of tubes in which the heat exchange occurs—of the multi-tubular heat exchanger is plunged into the pyrolysis furnace. Although this method is advantageous with regard to obtaining a high rate of heat recovery, coking still tends to occur and maintenance and cleaning of the distribution chamber are difficult.

It has also been attempted to prevent accumulation of coke deposits by using a multi-tubular indirect quick-cooling heat exchanger in which the space velocity in the distribution chamber is maintained at above 20 kg/m$^3$ per sec. to markedly shorten the residence time. However, the formation of coke deposits was still not completely prevented and this technique has not proved suitable for continuous and stable operation over extended periods of time. Furthermore, large pressure losses in the distribution chamber which result in increased reaction pressure in the pyrolysis reaction tube directly connected thereto, adversely affect the pyrolysis reaction.

The following patents are representative of the prior art suggestions for means for preventing coke build-up from occurring in the production of olefins by pyrolysis of hydrocarbons: U.S. Pat. Nos. 2,750,434 to Krejci, 2,791,549 to Jahnig, 3,270,077 to Tsutsmui et al., 3,392,211 to Buschmann et al. 3,414,632 to Buschmann et al., 3,416,598 to Dorn and 3,574,781 to Racine et al.; and British Pat. No. 1,087,512 assigned to Badische Anilin-& Soda-Fabrik Aktiengesellschaft.

The experience of the inventors of the subject application has shown that prevention of coking in the industrial manufacture of ethylene, propylene, etc. by the pyrolysis of ethane, propane, butane, pentane, etc. or low boiling hydrocarbons having a volumetric average boiling point of below 90° C., becomes a substantial problem at the portion of the apparatus connecting the reaction tube with the quenching device and at the portions of the quenching device where the mass velocity is below 50 kg/m$^2$ per sec.

Industrial pyrolysis and quick-quenching systems contain portions which do not contribute to cooling. These portions include, for example, the path between the reaction tube outlet port and the place in the quenching device where high-temperature cracked gas is quickly cooled, i.e. the connection tube simply connecting the reaction tube outlet port and the quenching device, and the portion which distributes or transfers the cracked gas into the positions where quenching takes place. In a multi-tubular indirect heat exchanger, these places can include the connection tube connecting the reaction tube outlet port with the heat exchanger and the distribution chamber which distributes the cracked gas into a plurality of tubes at the entrance of the heat exchanger. In the present specification, the portions which do not contribute to the cooling of high-temperature cracked gas between the above-mentioned reaction tube outlet port to the area where high-temperature cracked gas is cooled, are referred to as "transfer portion of the quenching device" or more simply, as "transfer portion".

Coke formation which impairs stable operation of the pyrolysis reaction is generally the result of undesireable secondary reaction taking place in the high-temperature cracked gas at the transfer portion where cooling of the cracked gas is not effected, and particularly, at those portions where the mass velocity is low. Further, coking will also be promoted when the volumetric average boiling point of the raw material is low, or when the residence time of cracked gas at the transfer portion is long, or when the cracking conditions are severe and when the mass velocity of the cracked gas is small.

The formation of coke deposits adhering to the walls of transfer portions has presented a serious impediment to making the pyrolysis reaction industrially feasible. For example, when operation of the pyrolysis furnace and quenching device is halted, differences in thermal expansion caused by coke adhered to the metallic members forming the connecting parts of the quenching devices results in development of stress, and often results in breakage of metallic members. Formation of coke deposits which remain adhered to the walls of the connecting parts in quenching devices, "chokes" the quenching devices, causing increased pressure losses in the quenching device, i.e. increased pressure at the outlet port of the pyrolysis furnace, thereby lowering the recovery of useful cracked gas and further accelerating the coking rate in the pyrolysis reaction tubes.

The present inventors do not believe that prior to the present invention, any method was completely successful in preventing the build-up of coke in the transfer portion to avoid the above-mentioned difficulties. As previously mentioned, attempts to prevent the formation of coking by increasing the mass velocity of gas at the transfer portion has caused increased pressure loss at the transfer portion as well as increased reaction pressure in pyrolysis reaction tube connected to the quenching device, thereby adversely affecting the pyrolysis reaction.

Therefore, the build-up of excess coke deposits at the transfer portions where mass velocity of the high-temperature cracked gases is below 50 kg/m$^2$ per sec., is now imposing the most difficult problem preventing the industrial scale application or the manufacture of olefins by pyrolysis of low-boiling hydrocarbons.

Therefore, it is an object of this invention to provide a quenching method which can prevent the formation of coke deposits, and solve all of the above-mentioned difficulties without increasing mass velocity of the cracked gas at the transfer portions.

After extensive research, the present inventors have now found that coking can be prevented completely by maintaining the metal surfaces where cracked gas at a temperature above 600° C. passes, at a temperature of below 450° C., regardless of raw materials, cracking conditions, cooling rate (residence time) of the cracked gas, or flow rate (mass velocity) of the cracked gas.

Therefore, according to the present invention, an improved method for manufacturing olefins such as ethylene and propylene, etc. by pyrolyzing hydrocarbons, such as ethane, propane or butane, etc. which are gaseous at room temperature and atmospheric pressure or liquid hydrocarbons having a volumetric average boiling point of below 90° C., without adding oxygen and without being accompanied by the burning of the hydrocarbons and with dilution steam in a pyrolysis furnace, at a temperature range from 750° to 900° C., followed by quick quenching in a multi-tubular quenching heat exchanger is provided. This improvement comprises maintaining the metallic surfaces of the transfer portions from the outlet portion of the pyrolysis reaction tube to the area in the quenching device where the cracked gas is cooled quickly and which metallic surfaces come into contact with cracked gases at a temperature above 600° C. and flowing at a mass velocity of below 50 kg/m$^2$ per sec., at a temperature below 450° C., by indirectly contacting the metallic surfaces with an aqueous cooling medium flowing through cooling coils in the transfer portion.

As mentioned above, in quickly cooling the cracked gases of low boiling hydrocarbons, coke that will cause troublesome problems is accumulated on the transfer portions only where their mass velocity is below 50 kg/m$^2$ per sec. Therefore, those portions where the mass velocity exceeds 50 kg/m$^2$ per sec. need not be maintained at a temperature below 450° C., although it is within the scope of the present invention to do so.

Examples of gaseous hydrocarbons which can be pyrolyzed and quickly cooled by the method of this invention include, for example, ethane, propane, butane, etc. Examples of liquid hydrocarbons having a volumetric average boiling point of below 90° C. which may be used in the subject invention, include, for example, the low boiling naphtha fraction of petroleum.

In the present invention, it is essential that the metallic surfaces of the transfer portions which come into contact with the cracked gas having a temperature above 600° C. and flowing at a mass velocity of below 50 kg/m$^2$ per sec., are maintained at a temperature below 450° C.

The present invention will now be described by the following detailed description and accompanying drawings in which:

FIG. 1 (b) is a flow sheet showing a modification of the method of the present invention;

FIG. 3 (b) is a detailed schematic diagram showing the construction of a modified multi-tubular heat exchanger in which a water-cooled jacket is used in place of water-cooled coils;

Figure 1A:
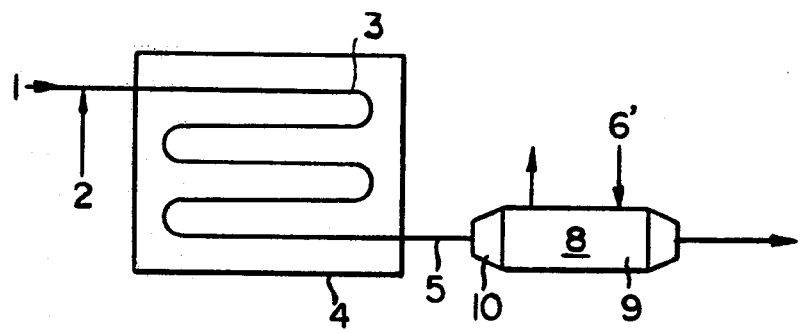
FIG. 1 (a) is a flow sheet illustrating one embodiment of the present invention.
Figure 1B:
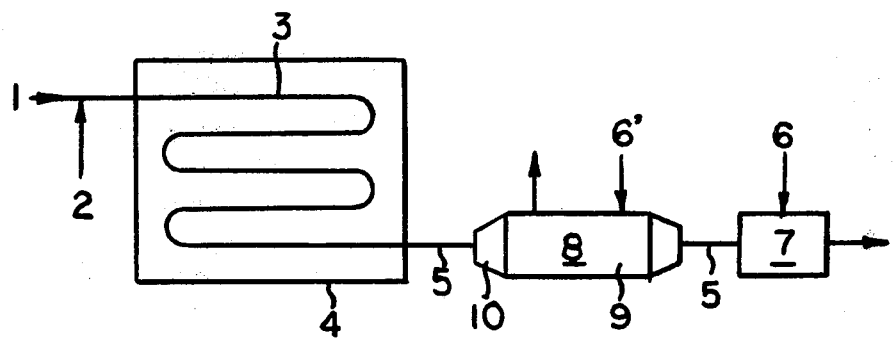
Figure 2:
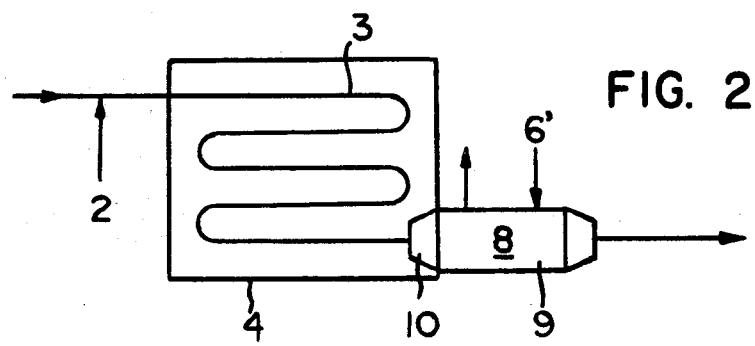
FIG. 2 is a flow sheet showing an example of the cracked gas quenching method of the type in which the distribution chamber of the multi-tubular heat exchanger is plunged into the pyrolysis furnace.
Figure 3A:
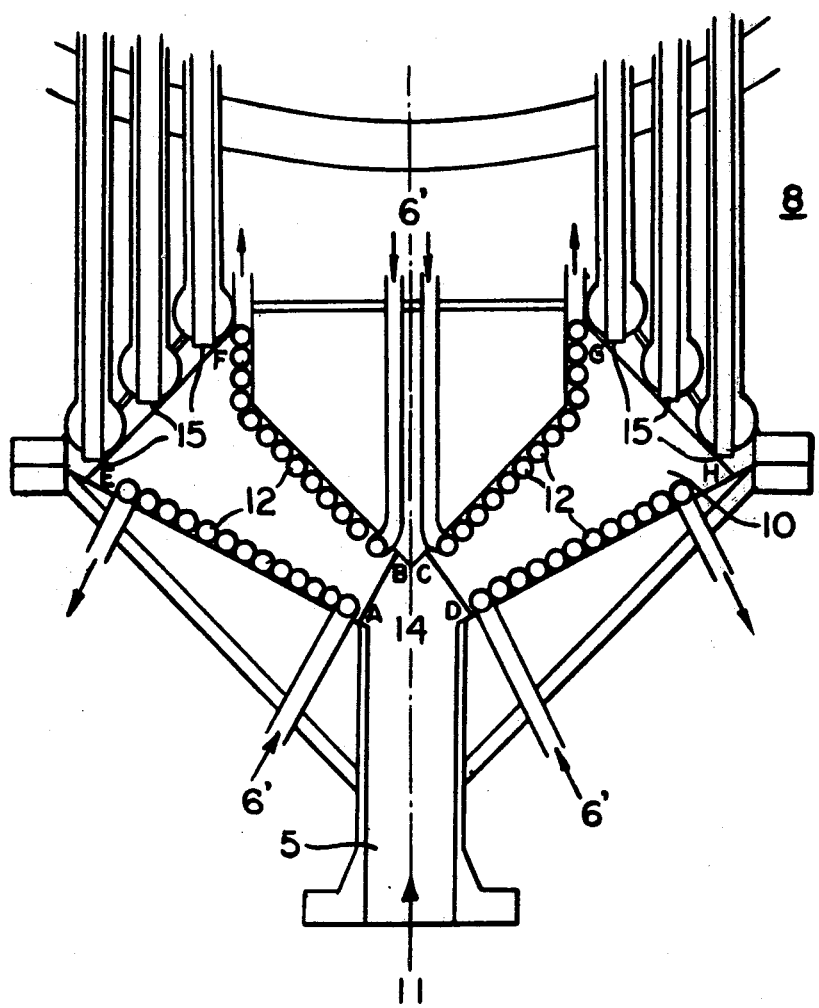
FIG. 3 (a) is a detailed schematic diagram showing the construction of a multi-tubular heat exchanger used in the improved process of the subject invention.
Figure 3B:
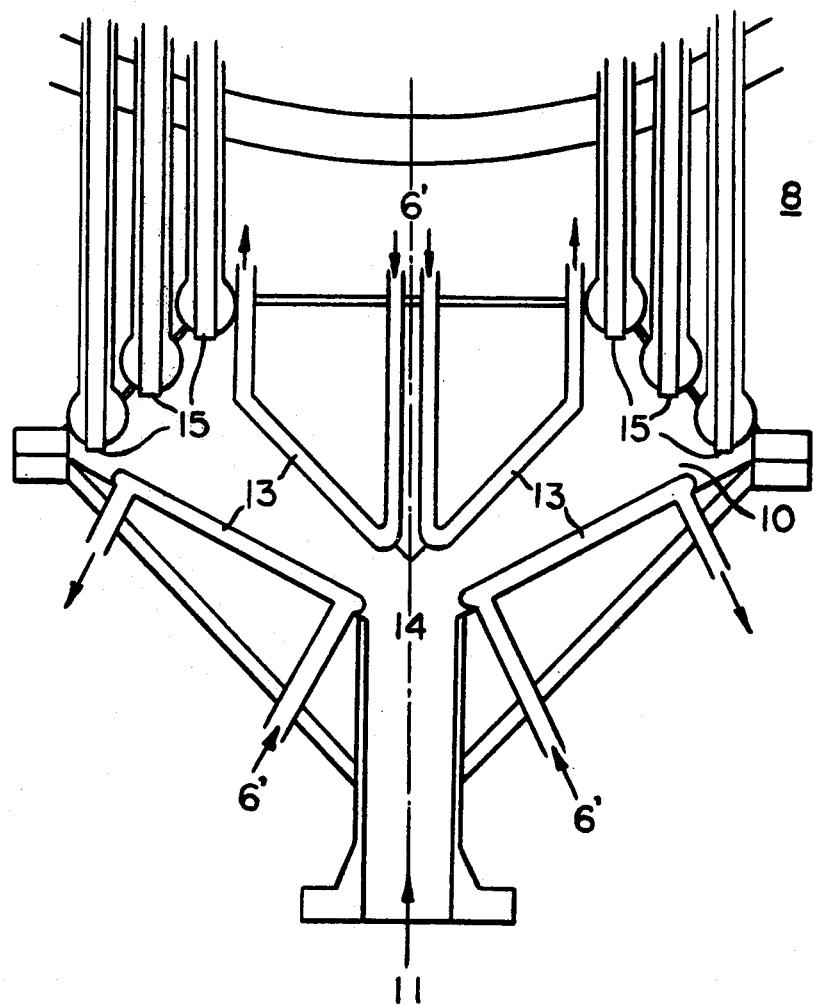

Referring to FIG. 1 (a), the raw material hydrocarbon 1 is admixed with steam 2 and passed to the pyrolysis furnace 4 where it is pyrolyzed at a temperature ranging from 750° to 900° C. in the reaction tube 3. The formed cracked gas passes through the connection tube 5 to the indirect heat exchanger 8 where it is cooled rapidly within a brief period of time to a temperature of 450° C. or lower by the coolant 6. Water is usually used as the coolant and is recovered as high-pressure steam. The metallic surfaces of the connection tube 5 and distribution chamber 10 of the indirect heat exchanger 8 where the mass velocity is below 50 kg/m$^2$ per sec. are lowered to a temperature below 450° C. The cooling can be effected by a water-cooled coil 12 which cools the inside of the distribution chamber 10 as shown in FIG. 3 (a), or by a water-cooled jacket 13 as shown in FIG. 3 (b).

It is also within the scope of this invention to combine the multi-tubular indirect heat exchanger with a direct flow of coolant in a quenching device 7 as shown in FIG. 1 (b).

The following examples are presented to illustrate concrete embodiments of the present invention without intending to imply any limitations to the scope of the subject invention.

In the following examples, the temperatures are measured by a thermocouple. The mass velocity represents the weight of fluid (kg/m$^2$ per second) flowing through the cross-sectional area across the axis of the flow passage per unit of time.

Also, the volumetric average boiling point of the raw materials is given by the equation:

$$\frac{t_{10} + t_{30} + t_{50} + t_{70} + t_{90}}{5}$$

where, $t_{10}$, $t_{30}$, ... represent temperatures (in degrees C.) where ASTM distillation fractions are 10% by volume, 30% by volume, etc.

EXAMPLE 1

A high-temperature cracked gas of the composition shown in Table 3 obtained by pyrolyzing the gaseous hydrocarbons of the composition shown in Table 1 under the cracking conditions of Table 2, heated at 830° C., at a pressure of 1.0 kg/cm²G at the furnace outlet port, was quickly cooled through the multi-tubular quenching heat exchanger, part of which is shown in FIG. 3 (a) to a temperature of 340° C. using water at a temperature of 320° C. In this example, the metallic inner surface of the distribution chamber 10 that comes into contact with cracked gas from the heat exchanger inlet port 14 to a distribution conduit inlet port 15, are wound over its upper and lower surfaces with a water-cooled tube 12 of one inch diameter to a 12-layered spring form, and water of 15 kg/cm²G, 100° C., was passed through the cooling tube to continue normal operation while maintaining the surfaces of the distribution chamber at a temperature below 450° C.

The mass velocity through the connection tube from the pyrolysis reaction tube to the heat exchanger was 170 kg/m² per sec., in average, and the mass velocity in the distribution chamber ranged from 170 to 8 kg/m² per sec., depending on the specific location, but most of which was below 50 kg/m² per sec.

As a result, no coking was formed in the transfer portions (no coke was formed through 90 days operation, no pressure rise at the furnace outlet port, or no degradation in cracked gas composition at the furnace outlet port), and the operation was continued for about three months until operation at the plant was halted for the purpose of routine decoking in the pyrolysis reaction tube.

COMPARATIVE EXAMPLE 1

By using the same apparatus and under the same conditions as in Example 1, the operation was continued without flowing cooling water through the water cooled tube 12 and without trying to decrease the temperature at the metallic surfaces.

Figure 4:
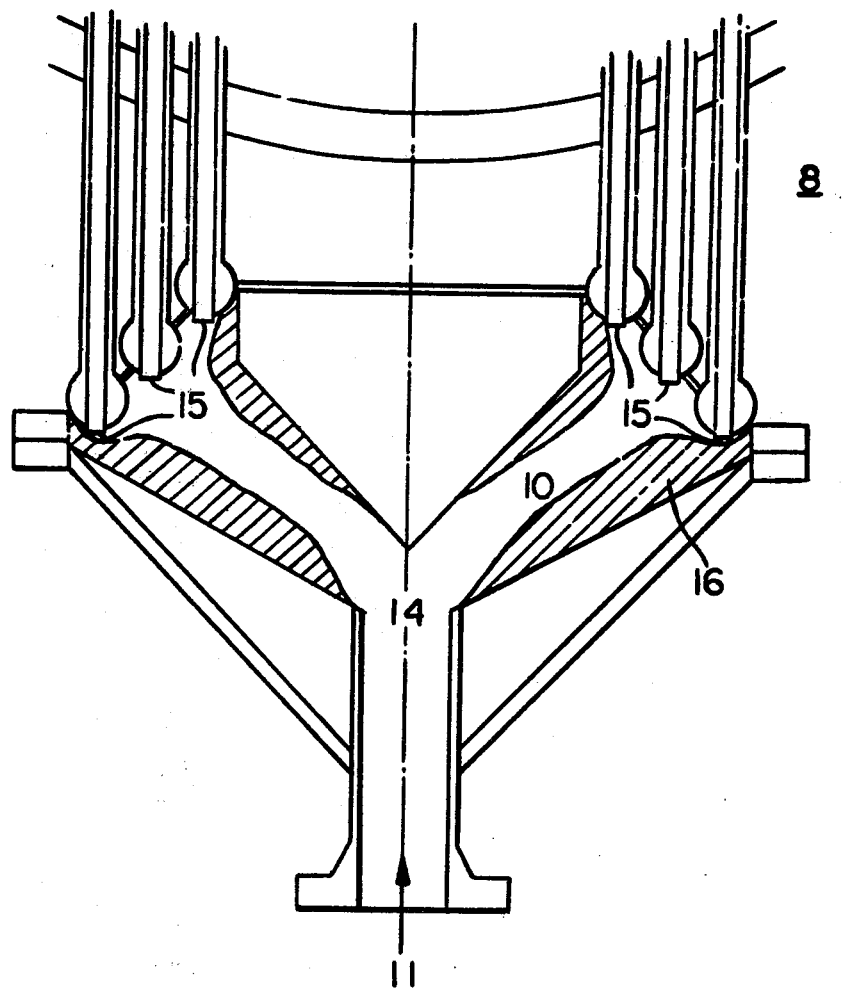
FIG. 4 is a schematic diagram of the apparatus used in the conventional method of pyrolysis showing accumulation of coke deposits.

As a result, as shown in FIG. 4, extreme coking 16 was developed at the portions in the distribution chamber where mass velocity is below 50 kg/m² per sec. and the metallic surfaces exceeded 450° C. (20 kg/m² formation of coke after 30 days continuous operation), choking the inlet port of the quenching heat exchanger cooling tube, and causing pressure loss in the quenching heat exchanger. Moreover, the pressure at the furnace outlet port was increased from 1.0 kg/cm²G to 1.7 kg/cm²G, forcing the operation of the plant to be halted after only 30 days operation.

Also, due to increased pressure loss in the quenching heat exchanger, the degradation rate of cracked gas composition at the furnace outlet port, 29 days after the start of operation, showed that the yield of ethylene was reduced by about 20%.

In the above example and comparative example, the inner diameter of the connection pipe 5 was 137mm. The cross-sectional area of the portions shown by lines $\overline{AB}$ and $\overline{CD}$ near the inlet of the distribution chamber 10 was 0.053m². The cross-sectional area of the portion shown by lines $\overline{EF}$ and $\overline{GH}$ near the distribution conduit inlet port 15 was 0.314m².

The mass velocities of the cracked gas present within connection pipe 5 and at the portions of the distribution chamber shown by lines $\overline{AB}$ and $\overline{CD}$ and lines $\overline{EF}$ and $\overline{GH}$ are calculated as follows. Based on the raw material hydrocarbon supply and steam ratio shown in Table 2, the supply of the steam diluent is $6.75 \times 0.34 = 2.295$ ton/hour. Therefor, the supply of the raw material plus steam to the pyrolysis furnace, and accordingly, the amount of the cracked gas to the multi-tubular quenching heat exchanger is $6.75 + 2.30 = 9.05$ ton/hour, i.e. 2.51 kg/sec. Accordingly, the mass velocity at the inside of the connection tube is mass velocity ÷ cross-sectional
area = $2.51 \div \pi/4 \times (0.137)^2 = 2.51 \div 0.0148 = 170$ kg/m².sec.

The mass velocity at the portions indicated by lines $\overline{EF}$ and $\overline{GH}$ is correspondingly $2.51 \div 0.314 = 8$ kg/cm².sec. At the portions indicated by lines AB and CD, the mass velocity is $2.51 \div 0.05 = 50$ kg/m².sec.

In Comparative Example 1, as illustrated in FIG. 4, coke accumulation increased in the direction corresponding to the lines $\overline{AB}$ and $\overline{CD}$ to the area shown by lines $\overline{EF}$ and $\overline{GH}$.

Table 1

| Raw Materials | Wt % |
|---|---|
| $C_2H_6$ | 96 |
| $C_2H_4$ | 1 |
| $C_3$ | 3 |

Table 2

| Cracking Conditions | | |
|---|---|---|
| Item | unit | |
| Raw material supply | T/H | 6.75 |
| Steam ratio | WT/WT | 0.34 |
| Cracking temperature | ° C. | 830 |
| Pressure at furnace outlet port | Kg/cm²G | 1.0 |

Table 3

| Cracked Gas Composition at the Furnace Outlet Port | | |
|---|---|---|
| Pressure at furnace outlet₂port (Kg/cm² . G) | | 1.0 |
| Yield (wt %) | $H_2$ | 3.0 |
| | $CH_4$ | 3.8 |
| | $C_2H_4$ | 42.5 |
| | $C_2H_6$ | 48.0 |
| | $C_3$ | 1.4 |
| | $C_4$ | 1.3 |

EXAMPLE 2

A high-temperature cracked gas of the composition shown in Table 7 obtained by pyrolysis of liquid hydrocarbons (more volatile naphtha) of the composition in Table 5 under the cracking conditions of Table 6, heated at 820° C., at a pressure of 1.0 kg/cm²G, at the furnace outlet port, was cooled to a temperature of 380° C. through a multi-tubular quenching heat exchanger, part of which is shown in FIG. 3 (a), using water of 120 kg/cm²G, 320° C. In this example, the metallic inner surfaces of the distribution chamber 10 that come into contact with cracked gas from the heat exchanger inlet port 14 to distribution conduit inlet port 15, are wrapped at its upper and lower surfaces with a water-cooled tube 12 of one inch diameter to a twelve-layered spring form, and water of 15 kg/cm², 100° C. was passed through the cooling tube to continue normal operating conditions and maintain the surfaces of the distribution chamber 10 at a temperature below 450° C.

The mass velocity through the connection tube from the pyrolysis reaction tube to the heat exchanger was 160 kg/m² per sec., in average, and the mass velocity in the distribution chamber ranged from 160 to 5 kg/m² per sec., depending on the location, but most of which was below 50 kg/m² per sec.

No coking was formed in the transfer portions through 120-days operation, no pressure rise at the furnace outlet port was observed, and the operation was continued for about 4 months until operation of the plant was halted for the purpose of routine decoking in the pyrolysis reaction tube.

Table 5

| | Raw materials and composition | |
|---|---|---|
| Distilled Properties | Specific weight | 0.68 |
| | IBP (° C.) | 25 |
| | 50 VOL % (° C.) | 80 |
| | EP (° C.) | 140 |
| | boiling point (° C.) | 80 |
| PONA Analysis | Parafin (wt. %) | 80 |
| | Naphthene (wt. %) | 15 |
| | Aromatic (wt. %) | 5 |

Table 6

| | Cracking conditions | |
|---|---|---|
| Item | Unit | |
| Raw material supply | T/H | 6.0 |
| Steam ratio | WT/WT | 0.5 |
| Cracking temperature | ° C. | 820 |
| Pressure at furnace outlet port | Kg/cm²:G | 1.0 |

Table 7

| Cracked gas composition at furnace outlet port. | | |
|---|---|---|
| Pressure at furnace outlet port (Kg/cm² · G) | | 1.0 |
| Yield (wt. %) | $H_2$ | 0.9 |
| | $CH_4$ | 15.6 |
| | $C_2H_4$ | 27.0 |
| | $C_2H_6$ | 5.0 |
| | $C_3$ | 16.5 |
| | $C_4$ | 10.0 |
| | $C_5$ | 25.0 |

COMPARATIVE EXAMPLE 2

Using the same apparatus and under the same operating conditions as in Example 2, the operation was continued without flowing cooling water through the water-cooled tube 12, without trying to decrease the temperature at the metallic surfaces.

Extreme coking 16 was formed in the distribution chamber where the mass velocity is below 50 kg/m² per sec., and the metallic surface temperature exceeded 450° C. The coke accumulation amounted to about 10 kg/m² after 50 days continuous operation resulting in choking of the inlet port of the quenching heat exchanger cooling tube and causing increased pressure loss in the quenching heat exchanger. Furthermore, the pressure at the furnace outlet port increased from 1.0 kg/cm²G to 1.5 kg/cm²G, forcing the operation of the plant to be halted after 50 days of operation.

Furthermore, due to increased pressure loss in the quenching heat exchanger, the degradation rate of cracked gas composition at the furnace outlet port 49 days after the start of operation was as listed in Table 8 below; the yield of ethylene was reduced by about 10%.

Table 8

| Change of cracked gas composition at the furnace outlet port | | | |
|---|---|---|---|
| Pressure at furnace outlet port (Kg/cm² · G) | | Start of operation 1.0 | 49 days after start of operation 1.5 |
| Yield (Wt. %) | $H_2$ | 0.9 | 1.0 |
| | $CH_4$ | 15.6 | 17.0 |
| | $C_2H_4$ | 27.0 | 25.0 |
| | $C_2H_6$ | 5.0 | 6.0 |
| | $C_2$ | 16.5 | 15.5 |
| | $C_4$ | 10.00 | 9.9 |
| | $C_5$ | 25.0 | 25.6 |

What is claimed is:

1. In a method of manufacturing olefins by the pyrolysis of hydrocarbons which assume gaseous state at room temperature under atmospheric pressure or liquid hydrocarbons having a volumetric average boiling point of below 90° C., without adding oxygen and without being accompanied by the burning of the hydrocarbons and with dilution steam in a pyrolysis furnace, at a temperature ranging from 750° to 900° C., followed by quick quenching in a multi-tubular quenching heat exchanger, the improvement which comprises maintaining the metallic surfaces of the transfer portions from the outlet portion of the pyrolysis reaction tube to the area in the said multi-tubular heat exchanger where the cracked gas is cooled quickly and which metallic surfaces come into contact with cracked gases at a temperature above 600° C. and flowing at a mass velocity of below 50 kg/m² per second, at a temperature below 450° C. by indirectly contacting said metallic surfaces with a water cooling medium flowing through cooling means in said transfer portion.

2. The method of claim 1 wherein the heat energy of the cracked gas is recovered as high-pressure steam.

3. The method of claim 1 wherein hydrocarbons which will be pyrolyzed are gaseous hydrocarbons selected from ethane, propane, butane, or a mixture of two or more kinds thereof.

4. The method of claim 1 wherein the hydrocarbon which will be pyrolyzed is a low boiling naphtha.

* * * * *